United States Patent
Gagliardoni et al.

(10) Patent No.: US 8,545,458 B2
(45) Date of Patent: Oct. 1, 2013

(54) PINCH CLAMP ASSEMBLY FOR AN INFUSION CASSETTE

(75) Inventors: Giancarlo Gagliardoni, Estado Miranda (VE); Giuseppe Antonio Nichetti, Pandino (CR) (IT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/379,195

(22) PCT Filed: Jun. 25, 2009

(86) PCT No.: PCT/EP2009/004601
§ 371 (c)(1), (2), (4) Date: Dec. 19, 2011

(87) PCT Pub. No.: WO2010/149187
PCT Pub. Date: Dec. 29, 2010

(65) Prior Publication Data
US 2012/0101437 A1    Apr. 26, 2012

(51) Int. Cl.
*A61M 5/175* (2006.01)
*A61M 5/142* (2006.01)
*F04B 43/08* (2006.01)

(52) U.S. Cl.
USPC ......... 604/250; 604/151; 604/153; 417/477.2

(58) Field of Classification Search
USPC ................. 417/477.2; 251/10; 604/34, 250, 604/131, 151, 153
See application file for complete search history.

(56) References Cited

U.S. PATENT DOCUMENTS

| 4,689,043 A | 8/1987 | Bisha |
| 5,203,056 A | 4/1993 | Funk et al. |
| 2007/0265559 A1 | 11/2007 | Kunishige et al. |

FOREIGN PATENT DOCUMENTS

| CN | 2925508 | 7/2007 |
| CN | 101035592 | 9/2007 |
| EP | 1557187 | 7/2005 |
| TW | 200613023 | 5/2006 |
| WO | 9630679 | 10/1996 |
| WO | 03011377 | 2/2003 |

OTHER PUBLICATIONS

PCT International Search Report for Application No. PCT/EP2009/004601 with a Mailing Date of Mar. 16, 2010. 4 Pages.

*Primary Examiner* — Nicholas Lucchesi
*Assistant Examiner* — Benjamin Koo
(74) *Attorney, Agent, or Firm* — K&L Gates LLP

(57) ABSTRACT

A pinch clamp assembly for engaging a tube with an enteral feeding or infusion pump adapted to feed nutritionals or to infuse medical solutions to a patient, is provided comprising a base (1) comprising holding means (3) for holding a pumping section (10) of the tube in operative engagement with the base (1) and supporting means (5) for supporting a connector (6), a clamping element (7) having clamping surfaces engageable with the pumping section (10) and moveable between an open position allowing flow of fluid through the pumping section (10) and a closed position, a cover element (8) for slidable engagement with the clamping element (7) and the connector (6), the cover element (8) being removable from the pinch clamp assembly, wherein the cover element (8) is mountable to or dis-mountable from the clamping element (7) and the connector (6) only when the clamping element (7) is in the closed position, wherein in the mounted position of the cover element (8) the clamping element (7) can be brought into the open position and the connector (6) cannot be removed from the assembly.

16 Claims, 10 Drawing Sheets

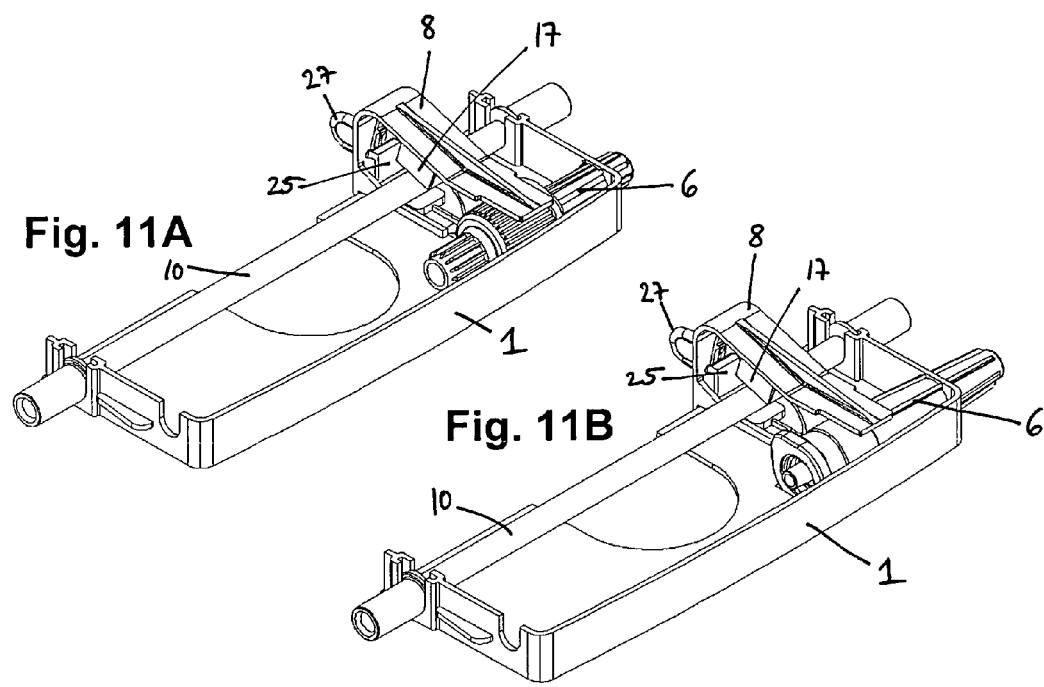
Fig. 11A
Fig. 11B
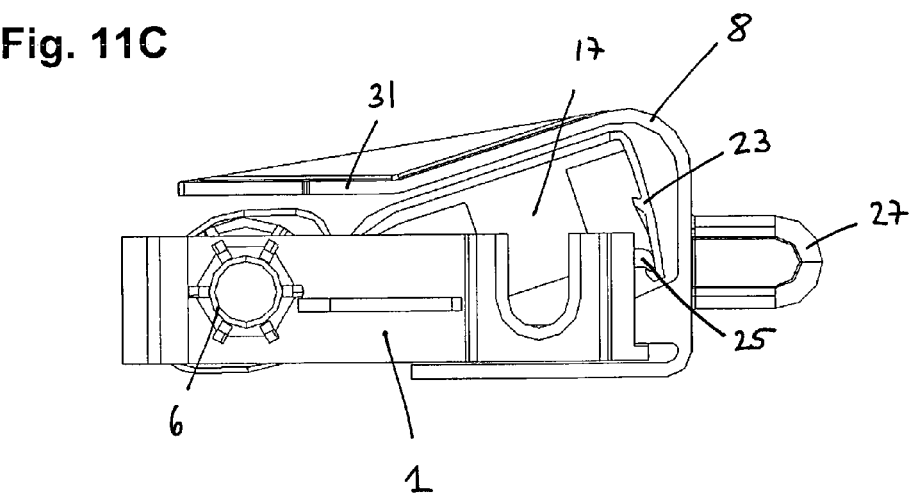
Fig. 11C

PINCH CLAMP ASSEMBLY FOR AN INFUSION CASSETTE

CROSS REFERENCE TO RELATED APPLICATIONS

The present application is a National Stage of International Application No. PCT/EP2009/004601, filed on Jun. 25, 2009, the entire contents of which are being incorporated herein by reference.

BACKGROUND OF THE INVENTION

The present invention relates to a pinch clamp assembly for engaging a tube with an enteral feeding pump adapted to feed nutritionals or an infusion pump adapted or to infuse medical solutions to a patient. More particularly, the present invention relates to a pinch clamp assembly in the form of a cassette with a clamping element for use on enteral feeding sets or infusion sets and the like, wherein the clamping element prevents the free-flow of enteral formula through the enteral feeding set or of solutions through the infusion set unless the cassette and the clamping element are properly mounted in a housing or some other structure of an enteral feeding pump or infusion pump.

The use of infusion and feeding sets to administer solutions and food to a patient is well known in medical arts. Infusion and enteral sets are used for both enteral and parenteral application, respectively. For hygienic reasons the infusion and enteral sets must be disposed of immediately after use, making it single-use equipment which may be recycled afterwards. Enteral feeding pumps are used to provide the patient with nutrition and medication (formula) when they are unable, for a variety of reason, to eat normally. Parenteral (intravenous) solutions are provided to patients to ensure adequate hydration and to provide needed nutrients, minerals and medication. Often, the enteral or infusion set is placed in a free standing arrangement in which gravity forces the formula or solution into the patient. The rate at which the solution enters the patient can be roughly controlled by various clamps, such as roller clamps, which are currently available on the market.

In many applications, it is necessary to precisely control the amount of solution or formula which enters the patient. When this is the case, a regulating device such as an infusion pump, is placed along the infusion set to control the rate at which the solution is fed to the patient. In application where a pump etc. is used the clamps used to regulate flow are typically open to their fullest extent to prevent the clamp from interfering with the proper functioning of the pump. The clamp is opened with the expectation that the enteral feeding pump or infusion will control fluid flow through the enteral or infusion set. However, emergencies or other distractions may prevent the medical personnel from properly loading the enteral or infusion sets in the enteral feeding pump or the infusion pump. Furthermore, the enteral or infusion sets may be inadvertently dislodged from the pump during operation of the pump.

When the enteral or infusion set is not properly loaded in the pump and the clamp has been opened, a situation known as free-flow often develops. The force of gravity causes the solution or the formula to flow freely into the patient unchecked by the pump or other regulating device. Under a free-flow condition, an amount of solution or formula many times the desired dose can be supplied to the patient within a relatively short time period. This can be particularly dangerous if the solution contains potent medicine or the patient's body is not physically strong enough to adjust to the large inflow of solution or formula. Thus there is a need for a device that prevents a free-flow condition if the enteral or infusion set is not properly mounted in the pump or other regulation means. It is furthermore important that the device is tamper-resistant with regard to the generation of the free-flow condition. Another requirement for such enteral feeding or infusion sets is a long storage period which may be up to several years. Therefore a sticking and continuous deformation of the silicon tube is to be avoided which may result in a deviation of its regular flow properties when using it.

Several approaches have been taken to avoid the above mentioned free-flow situation one of which is disclosed in WO 96/030679 A1. Therein, a pinch clip occluder utilizes a clamping mechanism with at least one arm nested at least partially within a housing which serves as an adjustment mechanism by moving the arm between a position in which the arm occludes flow through an infusion set, and a position in which it allows free-flow through the infusion set. One problem related therewith is that the pinch clip occluder can still be manipulated in a way that the spring force may be countered by other external elements such as a squeeze, a fastener or the like. Furthermore, the metal spring inside the pinch clip occluder according to WO 96/030679 A1 is not made of plastic material thus preventing the possibility of being recycled together with the other plastic components. This makes the recycling process of the infusion set more tedious and thus more expensive. Another disadvantage of said infusion set including the pinch clip occluder is that mounting it to the infusion or enteral feeding pump is rather complicated, i.e. the silicon tube has to be positioned exactly in the recesses formed therefore and wrapped around the rotor unit etc. In addition, a major drawback of this known pinch clip occluder is that when the cap with the prone is left inside the pinch clip occluder to open the tube, a free-flow situation is caused even when the infusion set is not attached to the pump. U.S. Pat. No. 4,689,043 describes an IV tube activator for use with a peristaltic IV infusion pump comprising means that require the closure of a tube associated clamp upon engagement of the IV tube with the pump and upon any subsequent disengagement of the IV tube from the pump. This IV tube activator also represents a rather complicated structure and will not solve the problem of storage of the clamped silicon tube before using it in the infusion pump. Furthermore, setting up the infusion set with the IV tube activator is cumbersome and error-prone due to the many different components.

SUMMARY OF THE INVENTION

It is therefore the object of the present invention to provide a pinch clamp assembly for engaging a tube with an enteral feeding or infusion pump adapted to feed nutritionals or to infuse medical solutions to a patient, which comprises a relatively simple construction, ensures an anti-free-flow mechanism that works at all times, allows for a long time storage of the silicon tube and is uniform with regard to the used material in order to be easily recyclable.

This object is solved by the features of claim 1. Advantageous embodiments of the invention are subject of the sub-claims.

According to the invention, a pinch clamp assembly for engaging a tube with an enteral feeding or infusion pump adapted to feed nutritionals or to infuse medical solutions to a patient is provided with the following components: a base comprising holding means for holding a pumping section of the tube in operative engagement with the base and supporting means for supporting a connector, a clamping element having clamping surfaces engageable with the pumping section and moveable between an open position allowing flow of fluid through the pumping section and a closed position wherein the pumping section is occluded by the clamping element, and locking means adapted to engage with each other in the closed position and adapted to interact with releasing means external to the pinch clamp assembly so as to bring the clamping element from the closed to the open position, a connector for connecting the tube with a port on a patient, the connector being removable from the pinch clamp assembly, and a cover element for slidable engagement with the clamping element and the connector, the cover element being removable from the pinch clamp assembly. It comprises the features that the cover element is mountable to or dismountable from the clamping element and the connector only when the clamping element is in the closed position, that in the mounted position of the cover element the clamping element can be brought into the open position and the connector cannot be removed from the assembly, and that the clamping element is adapted to engage with the releasing means to release the clamping element to the open position when pinch clamp assembly is mounted to the enteral feeding or infusion pump and the cover element and the connector are removed.

Thereby, the free-flow condition is prevented when the pinch clamp assembly is in its delivery state because the connector which is to be connected to the port of the patient, is still part of the pinch clamp assembly. Before a user is able to remove connector from the assembly, the cover element must be removed from the assembly which in turn will cause the clamping element to go to its closed position preventing any flow through the pumping section of the silicon tube. Therefore, the free-flow condition is again prevented when the respective connectors are connected to the port on the one end and to the solution or formula container on the other end. In this state, i.e. after the removal of the cover element and the connector, the pinch clamp assembly may be inserted into the enteral feeding or infusion pump. When inserting the pump, the clamping element is opened due to the interaction of the releasing elements with the clamping element. However, there is no free-flow condition because the pumping section of the silicon tube is so tightly wrapped around the pumping mechanism (rotor unit) of the enteral feeding or infusion pump that a flow of solution through the silicon tube is prevented. Thus, a free-flow condition of an infusion set comprising the pinch clamp assembly according to the present invention is avoided at all times, in particular before its first use.

Other advantages of the pinch clamp assembly according to the invention are that the assembly may be stored for a long time such as five years in its delivery state because the clamping element is in its open position. Also the anti-free-flow mechanism is an integral part of the pinch clamp assembly avoiding any additional components.

It is to be noted that to bring the pinch clamp assembly into the delivery state, which is usually as an entire infusion or enteral feeding set wrapped in single poly pouch or blister package, the single components of the pinch clamp assembly have to be put together accordingly, thereby sliding the cover element over the clamping element which is brought to its closed position occluding the silicon tube. However, the period of time where the flow is occluded is only minimal because the releasing means are immediately applied to the cover element thereby releasing the clamping element to its open position.

The pinch clamp assembly of the present invention is also tamper-resistant because for a normal user it is impossible to open the clamping element with her or his hands when the cover element is removed. Only the intention to tamper with the assembly using suitable tools (which are usually not available to the medical personnel setting up enteral feeding or infusion sets) will open the clamping element.

Preferably the base and the clamping element are integrally formed. This enables a compact pinch clamp assembly and reduces the number of parts involved in fabrication.

In an advantageous embodiment the connector is an enteral spike, an IV (intravenous) spike, an enteral feeding adapter, an IV luer lock adapter or other enteral or IV component. All possible connectors known in the art of enteral feeding or infusion can be used.

In a preferred embodiment the base is formed as a cassette such that the pinch clamp assembly may be integrally mounted to the enteral feeding or infusion pump. A cassette provides a flat construction which is not bulky and yet comprises a compact format.

Preferably the cover element extends at least partly over the cassette. For example the cover element may only be as wide as the clamping element to minimize used material. It is, however, also possible that the cover element covers the entire cassette in order to provide maximum protection of the pumping section and the other components.

In a preferred embodiment the pinch clamp assembly made of recyclable plastic material such as thermoplastics, and that the pumping section of the tube is made of silicon or silicon replacement tubing. This enables a simple recycling procedure of this one-way and single-use equipment and avoids tedious sorting procedures.

In an advantageous embodiment the clamping element comprises first leg with a tube blocking portion, a second leg with a flat surface, a bending portion acting as a spring element, first locking means at the free end of the first leg and second locking means at the free end of the second leg, wherein the tube blocking portion and the flat surface may be pressed upon one another to squeeze the tube therebetween, and wherein the first and second locking means are engageable with each other in the open position or in the closed position.

In a preferred embodiment the clamping surfaces are uneven, corrugated or finned. Depending on the specific requirements of the silicon tubing, different set-ups of the clamping surfaces may be used. It is also possible to change the function of the first leg and the second leg.

Preferably the cover element comprises a generally U-shaped form with a lower leg, an upper leg and a bottom portion. In an even more preferred embodiment the lower leg of the cover element comprises a recess engageable with the second leg of the clamping element, and the inner surface of the upper leg of the cover element abuts with the upper surface of the first leg of the clamping element in the open position of the clamping element. This enables a stable structure which provides for good protection of the clamping mechanism and an improved handling. It is to be noted that reinforcement links may be provided to ensure a higher stability.

In an advantageous embodiment the bottom portion of the cover element comprises a handle and two recesses for engagement with the releasing means. The two recesses can be two holes which are only accessible by very thin pins so as to prevent a tampering of the opening mechanism. The handle provides an intuitive direction for removing the cover element.

Preferably the supporting means comprise a first recess for accommodating the connector and a second recess for accommodating the tube associated with the connector. In this way, the connector and the tube associated with it can be held tight within the assembly (or cassette). This enables a tidy and compact design of the assembly which makes the use of the infusion set easier for medical personnel.

According to another embodiment of the present invention an enteral feeding or infusion pump comprises a pinch clamp assembly as mentioned above, wherein the pump comprises releasing means adapted to engage with the clamping element.

Preferably the flow through the pumping section is only enabled when the pinch clamp assembly is mounted. This ensures that the anti-free-flow mechanism is only disabled when the pinch clamp assembly is entirely mounted to the infusion pump.

BRIEF DESCRIPTION OF THE DRAWINGS

The above object, features and advantages of the present invention will become apparent from a consideration of the following detailed description presented in connection with the accompanying drawings in which:

FIG. 11A, 11B show two preferred embodiments of the pinch clamp assembly according to the invention in their delivery status;

FIG. 11C shows a side view of the pinch clamp assembly of FIG. 11B;

DETAILED DESCRIPTION

Figure 1:
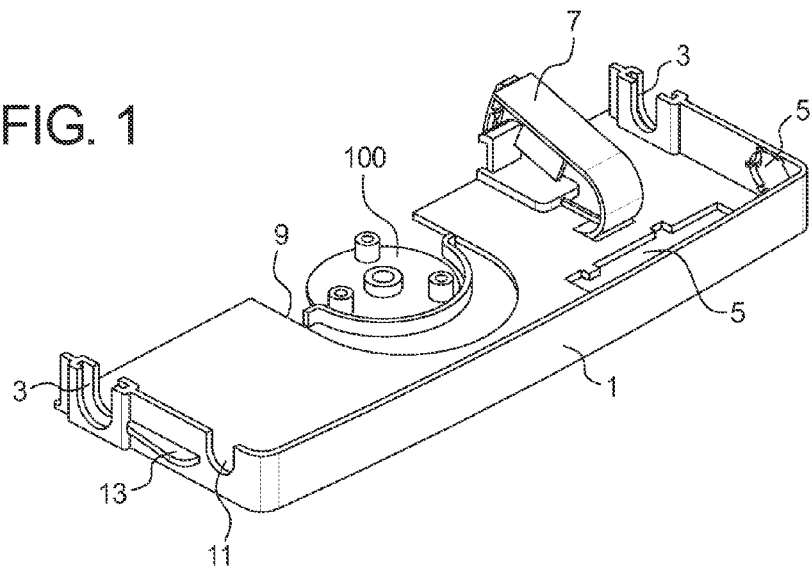
FIG. 1 shows a perspective view of a cassette according to a preferred embodiment of the pinch clamp assembly according to the invention.

FIG. 1 depicts a perspective view of the main component of a preferred embodiment of the pinch clamp assembly according to the invention which is comprised of cassette 1 forming the base of the assembly. Cassette 1 is configured generally rectangular and in a relatively flat structure. Cassette 1 comprises holding means 3 at opposing sides to support the pumping section of a silicon tube (not shown in this figure). Supporting means 5 are provided in cassette 1 in the form of a substantially round recess formed in a side wall of the cassette 1 and a further substantially rectangular recess formed in the ground plate of cassette 1. Supporting means 5 are provided to support a connector which will be described in more detail later. A central element of the pinch clamp assembly according to the invention is clamping element 7 which in the shown preferred embodiment is integral with cassette 1. The details of clamping element 7 will be described with reference to FIG. 2D and FIG. 2E. In the side wall opposing supporting means 5 there is provided a tube recess 11 for supporting the tube associated with the connector. In order not to over-complicate the figures with components not essential for the invention, the tube has been omitted at this point. Furthermore, the outer surfaces of the side walls of cassette 1 comprise side fins 13 which facilitate the sliding motion of the pinch clamp assembly when being mounted to an enteral feeding or infusion pump 100. The bottom portion of cassette 1 comprises a rotor unit recess 9 which is substantially in the shape of a half circle. When mounting the pinch clamp assembly according to the invention to the enteral feeding or infusion pump 100, the pins of the peristaltic rotor unit will fit into the space freed by the rotor unit recess 9.

Figure 2A:
FIG. 2A, 2B, 2C show a front view, plan view, and rear view, respectively, of the cassette shown in FIG. 1.
Figure 2B:
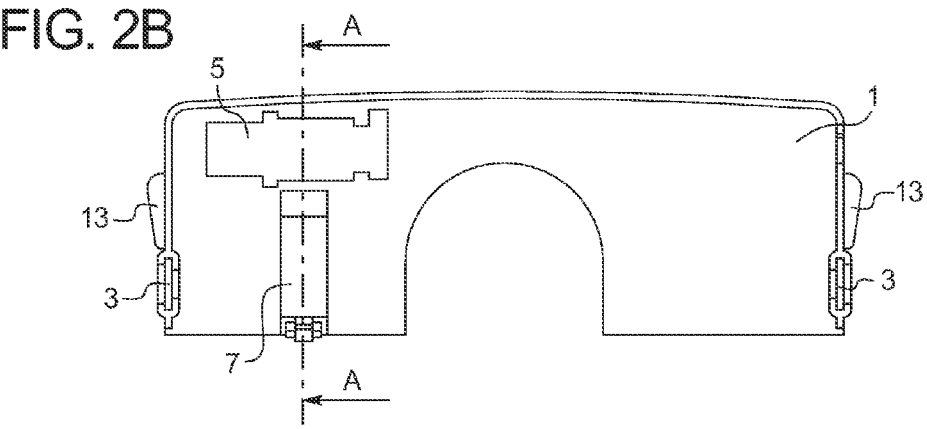
Figure 2C:
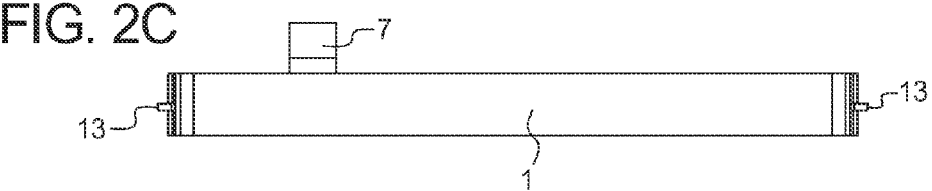

FIGS. 2A, 2B and 2C are front, plan and rear views of the pinch clamp assembly components of FIG. 1, wherein light numerals refer to like elements.

Figure 2D:
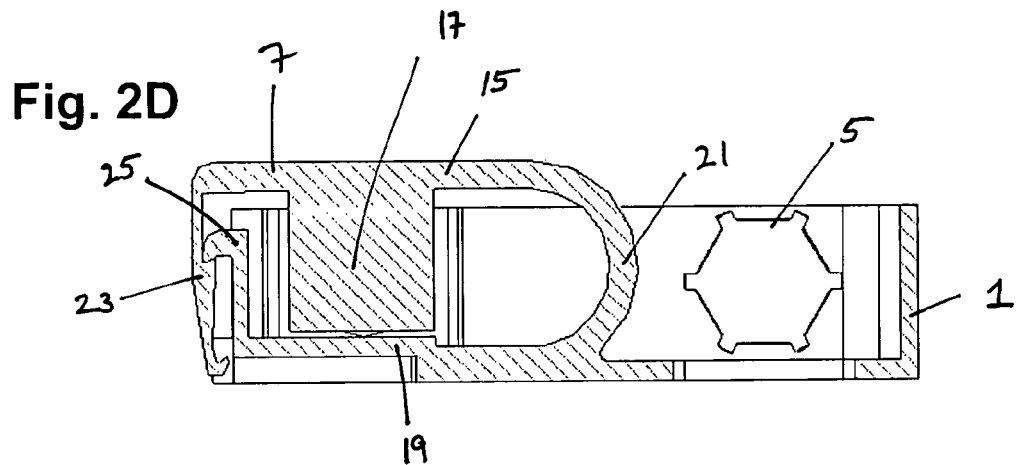
FIG. 2D, 2E show section views on the line A-A of FIG. 2B, wherein the clamping element is in the closed and open position, respectively.
Figure 2E:
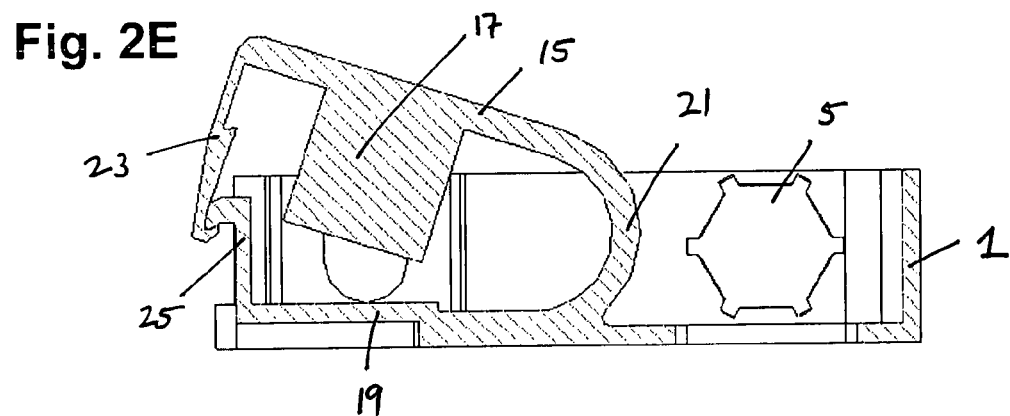

FIGS. 2D and 2E show an enlarged and sectional side view of the cassette 1 according to FIG. 1 wherein the clamping element 7 is in the closed (FIG. 2D) and the open position (FIG. 2E). Clamping element 7 generally, a first leg 15 with a tube blocking portion 17 in the form of a substantially rectangular plate which is attached to the first leg 15 at a substantially right angle. In the shown embodiment the second leg 19 of clamping element 7 is integrally formed with the mount plate of cassette 1. The linking element between first leg 15 and second leg 19 of clamping element 7 is bending portion 21 which acts as a spring element so that clamping element 7 may be moved from a tension-less open position to a closed position. At the free end of first leg 15 there is provided a first locking means 23 which extends in a substantially right angle towards the ground plate of cassette 1. First locking means 23 comprises to protrusions extending generally towards the bending portion 21. The counter part of first locking means 23 is second locking means 25 located at the free end of second leg 19. First locking means 23 and second locking means 25 are arranged such that they either engage with each other in a closed position (shown in FIG. 2D) or in the open position (shown in FIG. 2E).

Moving clamping element 7 from the open position to the closed position is simple: by pressing on the upper surface of a first leg 15 first locking means 23 is brought further down and will eventually engage at its upper protrusion with the protrusion formed in second locking means 25 against the spring force of bending portion 21 which results in a stable closed condition of clamping element 7. By briefly disengaging first locking means 23 and second locking means 25 clamping element 7 can be brought from the closed to the open position. This may be accomplished by bending second locking means 25 away from first locking means 23 into the direction of bending portion 21, i.e. substantially parallel to the plane of second leg 19. Since excess from the outside onto second locking means 25 is occluded by first locking means 23 particular tools have to be used to facilitate the releasing of the engagement of first and second locking means 23, 25.

It is to be noted, that other types of locking means may be used for clamping element 7 such as the mechanism used in a cable strap/tie wrap, magnetic closure mechanism or Velcro lock.

As can be seen from FIGS. 2D and 2E, the tube locking portion 17 will, in the closed position, almost touch the inner surface of the second leg 19 thereby squeezing the pumping section of silicon tube (not shown) in order to occlude the flow therethrough. In the shown embodiment the clamping surfaces of the tube blocking portion 17 and the second leg 19 are even. However, it is possible that the clamping surfaces are uneven, corrugated or finned so as to facilitate the squeezing function of the clamping element 7 depending on the characteristics of the silicon tube.

Figure 3:
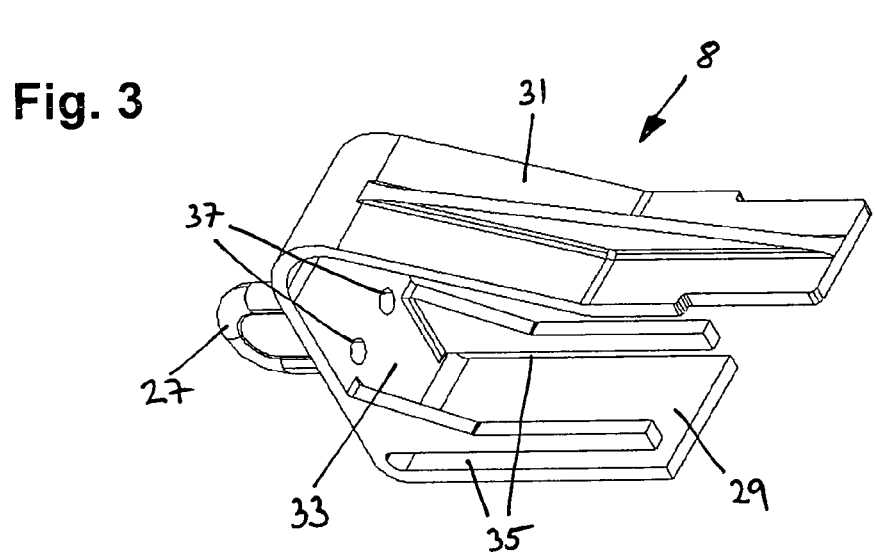
FIG. 3 shows a perspective view of a cover element of a preferred embodiment of the pinch clamp assembly according to the invention.
Figure 4A:
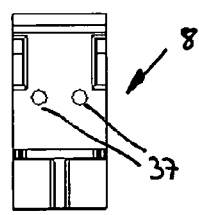
FIG. 4A, 4B, 4C, 4D show front view, plan view, rear view, and side view of the cover element shown in FIG. 3.
Figure 4B:
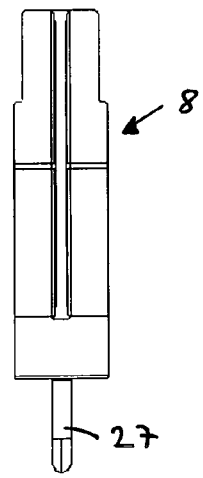
Figure 4C:
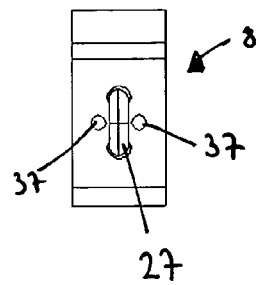
Figure 4D:
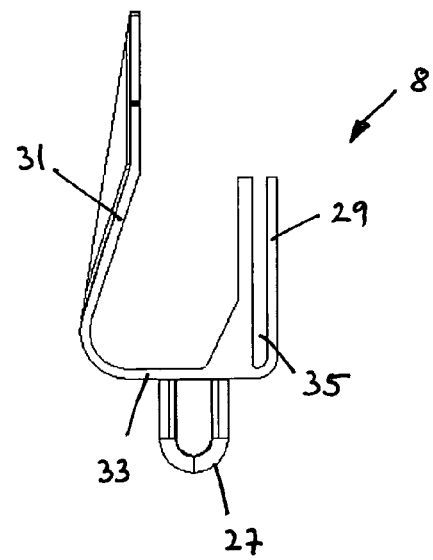

FIG. 3 shows a perspective view of a preferred embodiment of cover element 8 as part of the pinch clamp assembly according to the invention. Cover element 8 is generally U-shaped and comprises an upper leg 31, a bottom portion 33 and a lower leg 29. In the lower leg 29 two recesses 35 are formed which facilitate the mounting of cover element 8 onto clamping element 7 on cassette 1. It also prevents possible removal of cover element 8 to either side of the clamping element 7 and therefore ensures that the clamping element 7 is closed thus avoiding a free-flow-situation. The portion of upper leg 31 which is close to the bottom portion 33 is bend invert towards the direction of lower leg 29, wherein the free end of upper leg 31 is substantially parallel to lower leg 29. On the outer surface of bottom portion 33 there is provided a handle 27 substantially in the form of a semi-circle. The handle 27 is generally arranged in a plan rectangular to the plan of the lower leg 29 and upper leg 31. As can also be seen from FIGS. 4A, 4B, 4C, and 4D, which are front, plan, rear, and side views of the cover element shown in FIG. 3, there are provided holes 37 in the bottom portion 33 on either side of handle 27. The function of these holes 37 will be explained later on.

Figure 5A:
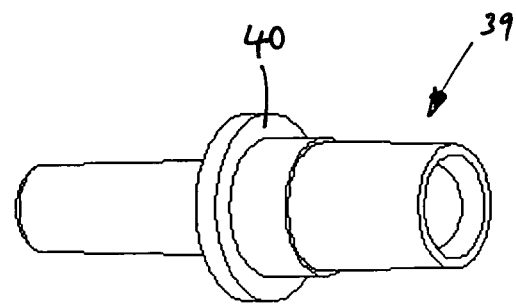
FIG. 5A, 5B show perspective views of a tube fitting element for a preferred embodiment of the pinch clamp assembly according to the invention.
Figure 5B:
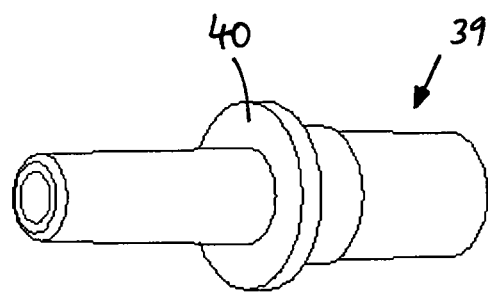

FIGS. 5A and 5B show perspective views of a tube-fitting element 39 which is adapted to hold the pumping section of the silicon tube and to fit into the holding means 3 provided in the cassette 1 of the pinch clamp assembly (see FIG. 1). In order to provide a good fit the tube fitting elements comprise a flange 40 which engages the recesses formed in the holding means 3 of cassette 1.

Figure 6:
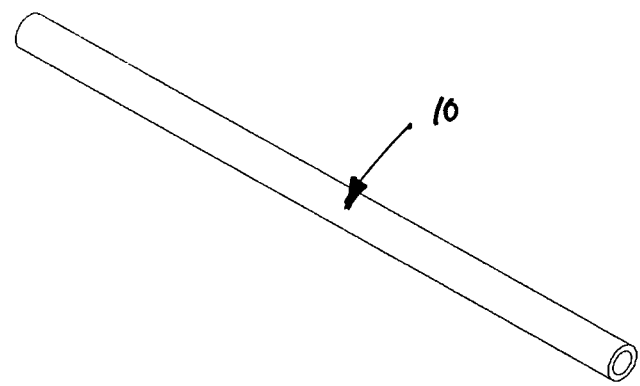
FIG. 6 shows a silicon tube of the preferred embodiment of the pinch clamp assembly according to the invention.

FIG. 6 shows the pumping section or silicon tube 10 which is arranged in the pinch clamp assembly according to the invention between the clamping surfaces of first leg 15 and second leg 19 and which is on either end tightly arranged at the respective ends of tube fitting elements 39. It is to be noted, that usually only the pumping section of the tubing portion of the entire infusion set is made of silicon, whereas the remaining portions of the tube are made of PVC (polyvinylchloride)

Figure 7:
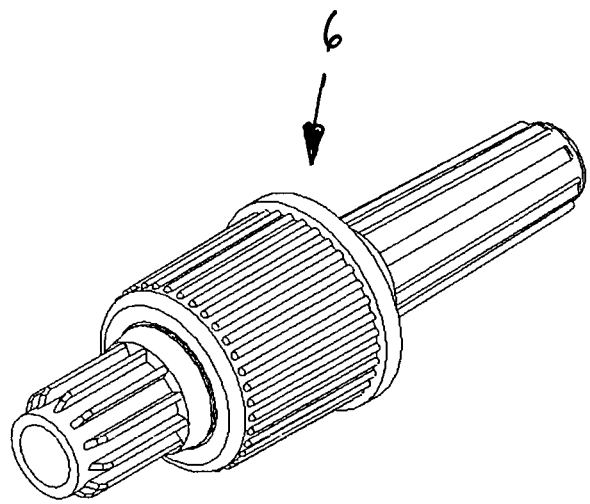
FIG. 7 shows a perspective view of an enteral universal spike with cover as part of the preferred embodiment of the pinch clamp assembly according to the invention.
Figure 8:
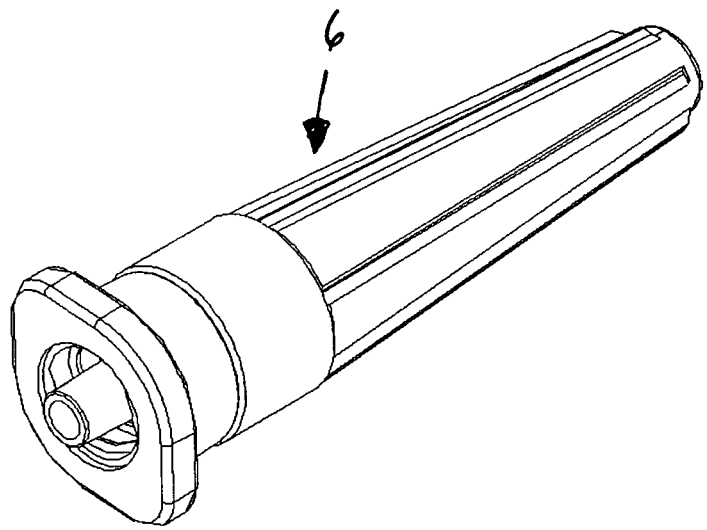
FIG. 8 shows an enteral adapter with cover of a further embodiment of the pinch clamp assembly according to the invention.

FIGS. 7 and 8 show two preferred embodiments of connector 6 as part of the pinch clamp assembly according to the invention. The embodiment of FIG. 7 shows a universal spike which may be used in a number of enteral feeding setups, the embodiment of FIG. 8 shows an enteral adapter which on one end comprises a female luer lock or a tapered fit. It is to be noted that in FIG. 7 the universal spike is on its shorter end directly connected to a tube, e.g. via solvent bonding.

The function of the pinch clamp assembly according to the present invention will now be described in more detail with reference to FIGS. 9A, 9B, 9C, 10A, 10B, 10C, 11 and 12.

Figure 9:
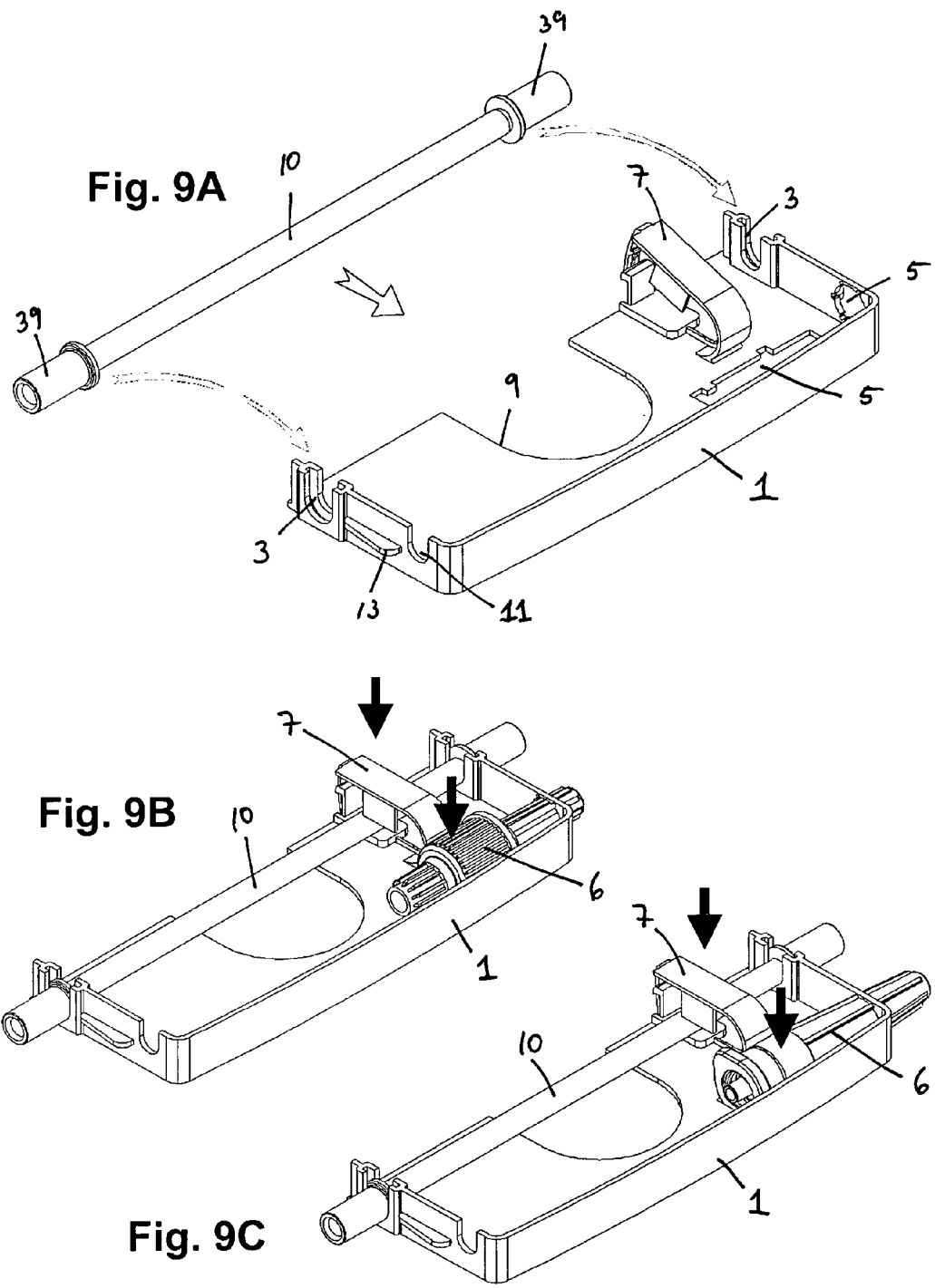
FIG. 9A, 9B, 9C show perspective views of some components of the preferred embodiment of the pinch clamp assembly according to the invention in different mounting statuses.

FIG. 9A shows in perspective view the first step when assembling the preferred embodiment of the pinch clamp assembly according to the invention. It is assumed that the cassette 1 is fabricated by injection moulding out of a thermoplastic material such as polypropylene, polystyrene, polyethylene or acrylnitril-butadien-styrene (ABS), also other suitable thermoplastics may be used. The pumping section 10 of the silicon tube has been associated with the two tube-fitting elements 39 and is now put into cassette 1. Before engaging the tube-fitting elements 39 into the holding means 3 of the cassette 1 the silicon tube 10 must be arranged between the first leg 15 and the second leg 19 of clamping element 7. For this purpose, the first locking means 23 and the second locking means 25 may be disengaged and the first leg 15 may be widely opened to receive silicon tube 10. Alternatively, the clamping element 7 can be kept in its open position and the silicon tube 10 may be slit between the clamping surfaces of the clamping element 7, and then associated with tube fitting element 39 which is then engaged with holding means 3. In the status after inserting silicon tube 10 into cassette 1 the pumping section is obviously not occluded. However, it is to be noted, that this status is merely an intermediate status while assembling the pinch clamp assembly of the invention.

FIGS. 9B and 9C show the next step of the assembly wherein the difference between FIGS. 9B and 9C lies only in the fact that the connector 6 is embodied in two different forms, the universal spike of FIG. 7 is shown in FIG. 9B and the enteral adapter of FIG. 8 is shown in FIG. 9C. The two arrows shall indicate the active movement with regard to two elements of the pinch clamp assembly: firstly, the clamping element 7 is brought into the closed position by pressing on the outer surface of the first leg 15 thereby occluding the pumping section of the silicon tube 10. The second movement is indicative for positioning the connector 6 within the supporting means 5 of cassette 1. As mentioned above, FIG. 9B shows the universal spike as connector 6, and FIG. 9C shows the enteral adapter as connector 6 supported within the cassette 1.

Figure 10:
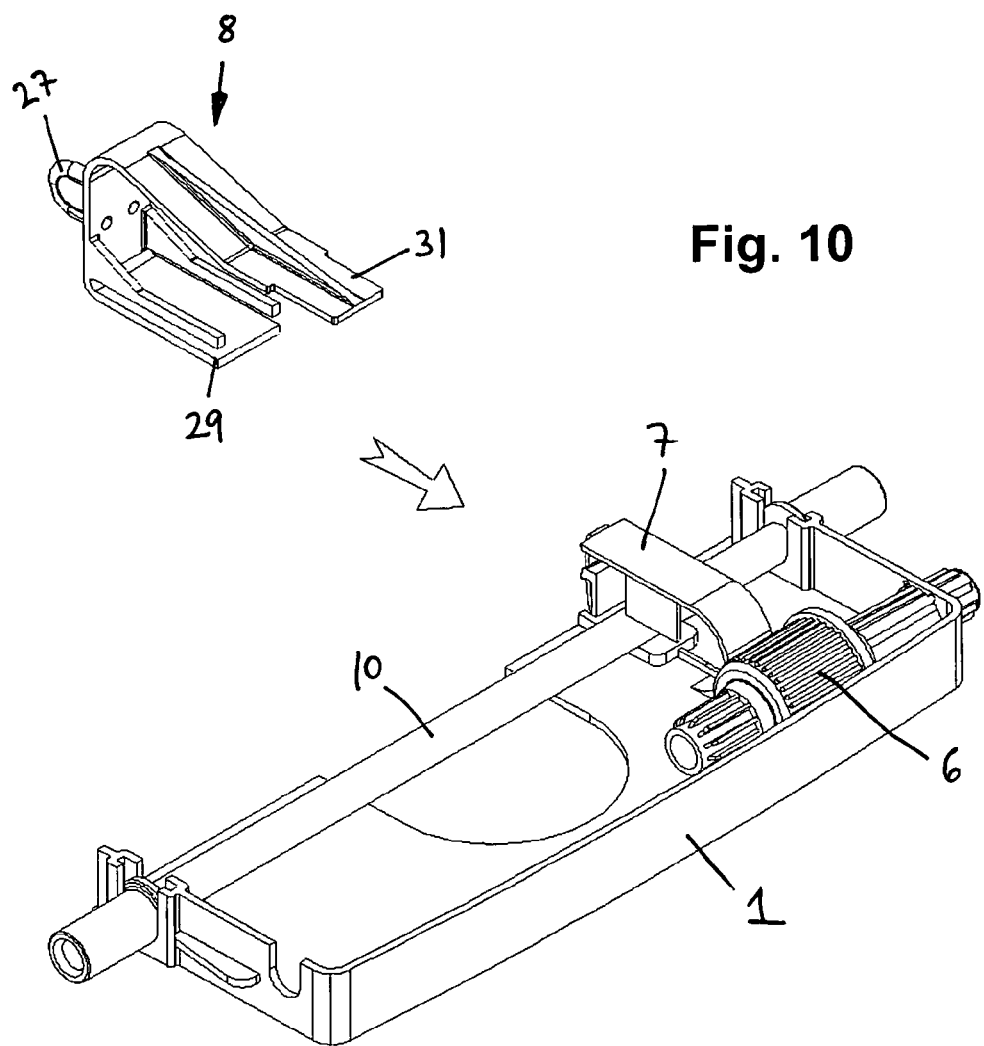
FIG. 10 shows a perspective view of a preferred embodiment of the pinch clamp assembly according to the invention in another mounting status.

The status depicted in FIGS. 9B and 9C is, again, an intermediate status during the assembly of the pinch clamp assembly according to the invention. It is necessary for the next step of the assembly which is mounding the cover element 8 to existing components of the pinch clamp assembly by sliding it over clamping element 7 which is in closed position until the open end up upper leg 31 comes to rest on the outer surface of connector 6 so as to hold it in its position within the supporting means 5. This step is shown in FIG. 10.

FIGS. 11A and 11B show perspective views of two preferred embodiments of the pinch clamp assembly according to the invention in their delivery status, after the cover element 8 has been mounted on the assembly and, more importantly, the clamping element 7 has been brought to the open position. The opening of the clamping element 7 is achieved by releasing the engagement between first locking means 23 and second locking means 25 of the clamping element 7 so as to open the area between the clamping surfaces and therefore to allow the silicon tube 10 to return to its relaxed sectional area. It is important to note, that in this delivery status of the pinch clamp assembly according to the invention the pumping section of silicon tube 10 is not deformed. However, in this delivery status there is no free flow situation of the pinch clamp assembly according to the invention because connector 6 is secured tightly within the assembly. Therefore, it is not possible for medical personnel to attach the connector 6 to a port of a patient which would result in a free flow condition. It is the key principle of the present invention that while the cover element 8 which functions as a key lock is mounted on the assembly, it is not possible to generate a free flow condition since the connector 6 is held tightly within the assembly and removing the cover element 8 from the assembly will automatically bring the clamping element to its close position and therefore occlude the flow through the pumping section of the silicon tube 10.

FIG. 11C shows a side view of the pinch clamp assembly of FIG. 11B with the clamping element 7 in its open position. Moving from the status of FIG. 10 to the status of FIGS. 11A, 11B and 11C requires that the engagement of first locking means 23 with second locking means 25 be released. This can be achieved by an external tool as part of the assembling process of the pinch clamp assembly according to the invention wherein this special tool pushes the second locking means 25 towards portion 21 of the clamping element 7 so as to release the hook-type engagement of the locking means. It is obvious that this releasing of the clamping element 7 cannot be accomplished easily, for example only with fingers. FIG. 11C also shows that the cover element 8 is very well fitted over cassette 1 even clamping element 7 so as to leave enough space for the relaxed first leg 15 of clamping elements 7 in the open position. On the other hand, the upper leg 31 of the cover element extends over the most part of the surface of connector 6 making it impossible to take connector 6 out of the assembly in this status.

It is to be noted that the pinch clamp assembly as shown in FIGS. 11A, 11B and 110 cannot be mounted to an enteral feeding or infusion pump as is. Before the mounting can take place, cover element 8 has to be removed thereby bringing clamping element 7 into the closed position. As can be seen again from FIG. 11C the removal of the cover elements will cause upper leg 31 of cover element 8 to slide over the upper surface of first leg 15 so as to bring first leg 15 further down so that finally first locking means 23 and second locking means 25 engage with each other in the closed position. In this embodiment it is important that the cover element 8 may only be removed from the assembly in one direction. The removal of cover element 8 is initiated by pulling handle 27 away from the pinch clamp assembly, and it is clear that removing the cover element will also give open access to connector 6 which can be taken out of the assembly and connected a port in order to set up the enteral feeding or infusion set. When mounting the pinch clamp assembly, with cover element 8 and connector 6 removed, to the enteral feeding or infusion pump the clamping element 7 is in its closed position thereby occluding the flow of liquid through the pumping section of silicon tube 10. The free flow condition is thus avoided. However, the occluded status of the pumping section of the silicon tube 10 must be released as soon as the cassette 1 with the other components of the pinch clamp assembly are mounted in the enteral feeding or infusion pump. The cassette shape of the base of the pinch clamp assembly facilitates the handling and the mounting of the assembly to the pump.

Figure 12:
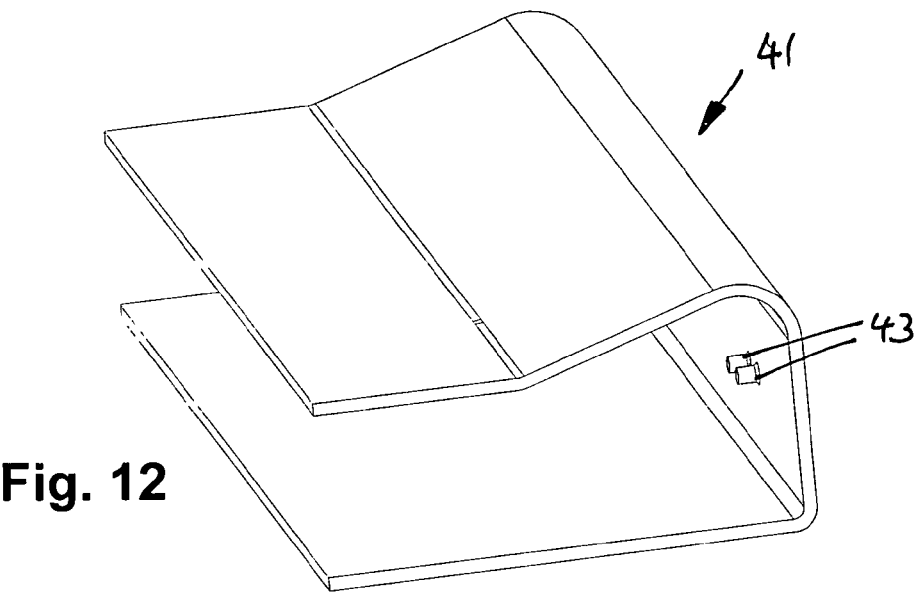
FIG. 12 shows a perspective view of an external releasing apparatus as part of an enteral feeding or infusion pump according to the invention.

FIG. 12 shows the external releasing apparatus 41 which is part of the enteral feeding or infusion pump 100. The external releasing apparatus 41 is substantially U-shaped similar to the cover element 8.

Figure 13:
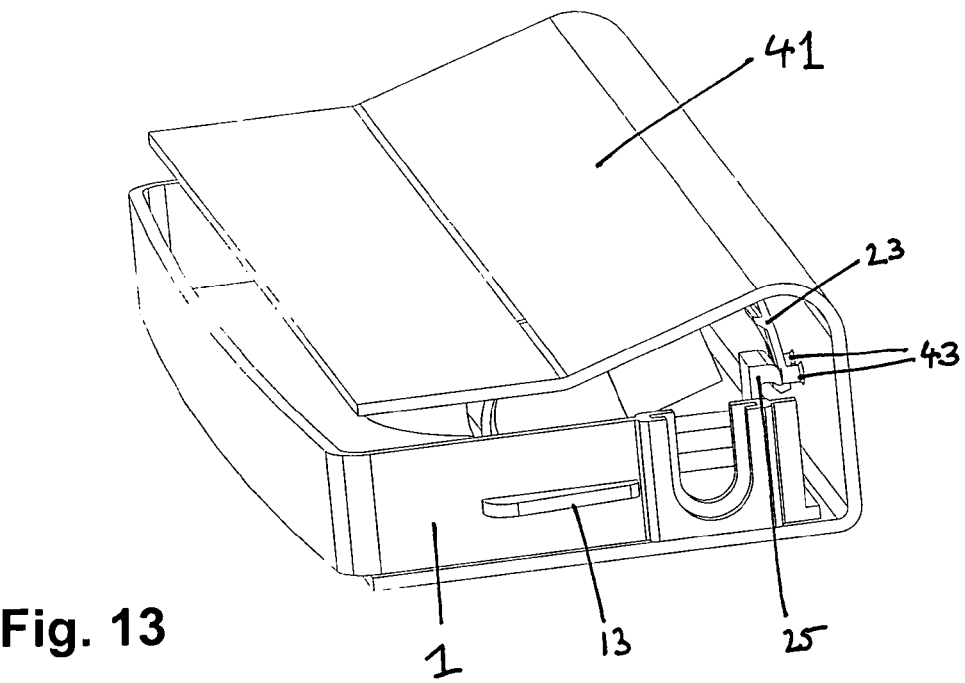
FIG. 13 shows a perspective view of a preferred embodiment of the pinch clamp assembly according to the invention in engagement with the external releasing apparatus of FIG. 12.

FIG. 13 shows a preferred embodiment of the pinch clamp assembly according to the invention in engagement with the external releasing apparatus 41. It can be seen that when cassette 1 is in fully mounted position within the enteral feeding or infusion pump 100, the locking means 23 and 25 will abut with the bottom section of the external releasing apparatus in the area of the pins 43. Since the width of second locking means 25 is larger than the width of first locking means 23 there is an area on either side of the first locking means 23 where the pins 43 can touch second locking means 25 and actually push second locking means 25 towards the bending portion of clamping element 7 so as to release the engagement between first and second locking means 23, 25.

In the above preferred embodiment of the locking and releasing mechanism has been described. It is to be noted, that other locking-releasing mechanisms are possible such as a magnetic solution or a solution with fastening means. All alternative solutions however should fulfill the central requirement which is that they are temper-resistant so that the clamping element 7 cannot be opened easily by hand or with tools which are easily available to medical personnel.

Figure 14A:
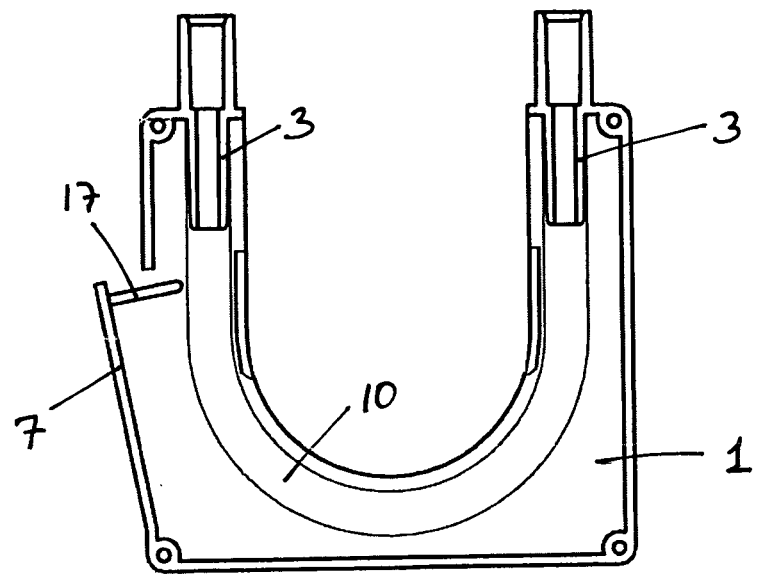
FIG. 14A, 14B show a plan view of a schematic structure of an alternative embodiment of the pinch clamp assembly of the present invention.
Figure 14B:
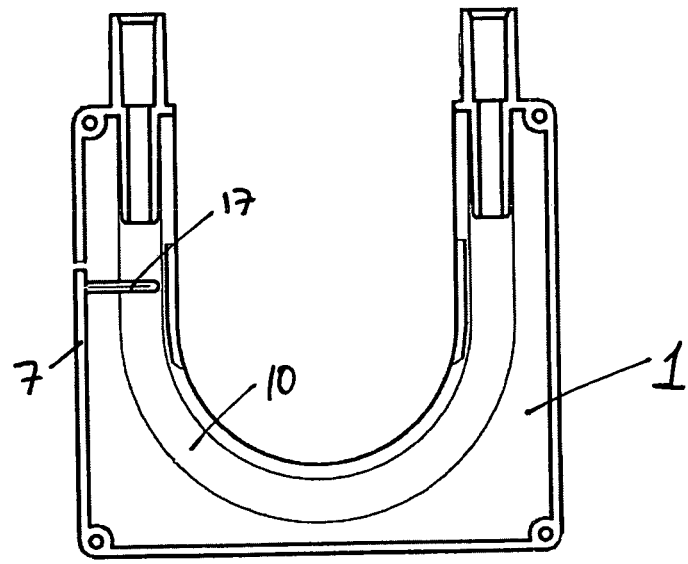

FIGS. 14A and 14B show an alternative to the preferred embodiment shown in the previous figures: a cassette structure 1 with holding means 3 being arranged parallel to each other surrounding a substantially semi-circular recess and with the pumping section 10 essentially following the outline of the semicircle may be provided. In this alternative configuration, the clamping element 7 may be located at the side of the cassette 1, with the opening and closing movement of clamping element 7 lying parallel to the pumping section plane, i.e. in FIG. 14A someone would have to push from the side of the cassette 1 to move the clamping element to the closed position shown in FIG. 14B. This allows for an even more compact configuration of the pinch clamp assembly.

With the subject-matter of the present invention a pinch clamp assembly for engaging a tube with an enteral feeding or an infusion pump adapted to feed nutritionals or to infuse medical solutions to a patient has been provided which comprises a relatively simply construction, ensures an anti-free-flow mechanism that works at all times, allows for a long time storage of the silicon tube and is uniform with regard to the used material in order to be easily recyclable.

The invention claimed is:

1. A pinch clamp assembly for engaging a tube with an enteral feeding or infusion pump adapted to provide solutions to a patient, the pinch clamp assembly comprising:

a base comprising a holder for holding a pumping section of the tube in operative engagement with the base and a support for supporting a connector;

a clamping element having clamping surfaces engageable with the pumping section and moveable between an open position allowing the flow of fluid through the pumping section and a closed position wherein the pumping section is occluded by the clamping element, and a first lock and a second lock adapted to engage with each other in the closed position and adapted to interact with a releasing apparatus external to the pinch clamp assembly so as to bring the clamping element from the closed to the open position;

a connector for connecting the tube with a port on a patient, the connector being removable from the pinch clamp assembly;

a cover element for engagement with the clamping element and the connector, the cover element being removable from the pinch clamp assembly;

the cover element is mountable to or dismountable from the clamping element and the connector only when the clamping element is in the closed position;

in the mounted position of the cover element the clamping element can be brought into the open position and the connector cannot be removed from the pinch clamp assembly; and the clamping element is adapted to engage with the releasing apparatus to release the clamping element to the open position when pinch clamp assembly is mounted to the pump and the cover element and the connector are removed.

2. The pinch clamp assembly according to claim 1, wherein the base and the clamping element are integrally formed.

3. The pinch clamp assembly according to claim 1, wherein the connector is selected from the group consisting of an enteral spike, an IV spike, an enteral feeding adapter, and an IV luer lock adapter.

4. The pinch clamp assembly according to claim 1, wherein the base is formed as a cassette such that the pinch clamp assembly may be integrally mounted to the pump.

5. The pinch clamp assembly according to claim 4, wherein the cover element extends at least partly over the cassette.

6. The pinch clamp assembly according to claim 1, wherein the clamping assembly is made of recyclable plastic material, and that the pumping section of the tube is made of silicon.

7. The pinch clamp assembly according to claim 1, wherein the clamping element comprises a first leg with a tube blocking portion, a second leg with a flat surface, a bending portion acting as a spring element, the first lock at the free end of the first leg and the second lock at the free end of the second leg, wherein the tube blocking portion and the flat surface may be pressed upon one another to squeeze the tube therebetween, and wherein the first and second locks are engageable with each other in the open position or in the closed position.

8. The pinch clamp assembly according to claim 7, wherein the lower leg of the cover element comprises a recess engageable with the second leg of the clamping element, the inner surface of the upper leg of the cover element abuts with the upper surface of the first leg of the clamping element in the open position of the clamping element.

9. The pinch clamp assembly according to claim 1, wherein the clamping surfaces have a structure selected from the group consisting of uneven, corrugated and finned.

10. The pinch clamp assembly according to claim 1, wherein the cover element comprises a generally U-shaped form with a lower leg, an upper leg and a bottom portion.

11. The pinch clamp assembly according to claim 10, wherein the bottom portion of the cover element comprises a handle and two recesses for engagement with the releasing apparatus.

12. The pinch clamp assembly according to claim 1, wherein the support comprises a first recess for accommodating the connector and a second recess for accommodating the tube associated with the connector.

13. A pump assembly comprising:
an enteral pump adapted to provide solutions to a patient;
a pinch clamp assembly for engaging a tube with the enteral feeding pump, the pinch clamp assembly comprising:
 a base comprising a holder for holding a pumping section of the tube in operative engagement with the base and a support for supporting a connector,
 a clamping element having clamping surfaces engageable with the pumping section and moveable between an open position allowing flow of fluid through the pumping section and a closed position wherein the pumping section is occluded by the clamping element, and a first lock and a second lock adapted to engage with each other in the closed position and adapted to interact with a releasing apparatus external to the pinch clamp assembly so as to bring the clamping element from the closed to the open position,
 a connector for connecting the tube with a port on a patient, the connector being removable from the pinch clamp assembly,
 a cover element for engagement with the clamping element and the connector, the cover element being removable from the pinch clamp assembly, the cover element is mountable to or dismountable from the clamping element and the connector only when the clamping element is in the closed position, in the mounted position of the cover element the clamping element can be brought into the open position and the connector cannot be removed from the pinch clamp assembly, and the clamping element is adapted to engage with the releasing apparatus release the clamping element to the open position when the pinch clamp assembly is mounted to the pump and the cover element and the connector are removed; and
a release mechanism adapted to engage with the clamping element.

14. The pump assembly according to claim 13, wherein flow through the pumping section is only enabled when the pinch clamp assembly is mounted thereon.

15. A pump assembly comprising:
an infusion pump adapted to provide solutions to a patient;
a pinch clamp assembly for engaging a tube with the infusion pump, the pinch clamp assembly comprising:
 a base comprising a holder for holding a pumping section of the tube in operative engagement with the base and a support for supporting a connector,
 a clamping element having clamping surfaces engageable with the pumping section and moveable between an open position allowing flow of fluid through the pumping section and a closed position wherein the pumping section is occluded by the clamping element, and a first lock and a second lock adapted to engage with each other in the closed position and adapted to interact with a release apparatus external to the pinch clamp assembly so as to bring the clamping element from the closed to the open position,
 a connector for connecting the tube with a port on a patient, the connector being removable from the pinch clamp assembly,
 a cover element for engagement with the clamping element and the connector, the cover element being removable from the pinch clamp assembly, the cover element is mountable to or dismountable from the clamping element and the connector only when the clamping element is in the closed position, in the mounted position of the cover element the clamping element can be brought into the open position and the connector cannot be removed from the pinch clamp assembly, and the clamping element is adapted to engage with the releasing apparatus to release the clamping element to the open position when the pinch clamp assembly is mounted to the pump and the cover element and the connector are removed; and
a release mechanism adapted to engage with the clamping element.

16. The pump assembly according to claim 15, wherein the flow through the pumping section is only enabled when the pinch clamp assembly is mounted thereon.

* * * * *